(12) United States Patent
Akamatsu et al.

(10) Patent No.: US 8,912,172 B2
(45) Date of Patent: Dec. 16, 2014

(54) SKIN EXTERNAL PREPARATION CONTAINING TRITERPENIC ACID

(75) Inventors: Hisashi Akamatsu, Yokohama (JP); Masashi Suzuki, Yokohama (JP); Yuji Sakai, Yokohama (JP)

(73) Assignees: Kuraray Co., Ltd., Okayama (JP); Pola Chemical Industries Inc., Shizuoka-Shi, Shizuoka (JP)

( * ) Notice: Subject to any disclaimer, the term of this patent is extended or adjusted under 35 U.S.C. 154(b) by 511 days.

(21) Appl. No.: 12/305,350

(22) PCT Filed: Apr. 24, 2007

(86) PCT No.: PCT/JP2007/058781
§ 371 (c)(1),
(2), (4) Date: Dec. 17, 2008

(87) PCT Pub. No.: WO2007/148474
PCT Pub. Date: Dec. 27, 2007

(65) Prior Publication Data
US 2009/0253663 A1    Oct. 8, 2009

(30) Foreign Application Priority Data

Jun. 19, 2006 (JP) ................................. 2006-169113

(51) Int. Cl.
| | | |
|---|---|---|
| *A61K 31/56* | (2006.01) | |
| *A61K 31/19* | (2006.01) | |
| *A61K 31/20* | (2006.01) | |
| *A61Q 19/00* | (2006.01) | |
| *A61Q 19/08* | (2006.01) | |
| *A61K 8/34* | (2006.01) | |
| *A61K 8/63* | (2006.01) | |
| *A61K 9/00* | (2006.01) | |

(52) U.S. Cl.
CPC ............... *A61Q 19/08* (2013.01); *A61Q 19/00* (2013.01); *A61K 31/56* (2013.01); *A61K 8/347* (2013.01); *A61K 9/0014* (2013.01); *A61K 8/63* (2013.01)
USPC .......................................... 514/171; 514/558

(58) Field of Classification Search
CPC ....................................................... A61K 31/56
See application file for complete search history.

(56) References Cited

U.S. PATENT DOCUMENTS

| | | | |
|---|---|---|---|
| 5,723,139 A | 3/1998 | Granger et al. | |
| 2003/0180234 A1* | 9/2003 | Love et al. ...................... | 424/59 |

FOREIGN PATENT DOCUMENTS

| | | | |
|---|---|---|---|
| JP | 02-049715 | | 2/1990 |
| JP | 08-165231 | | 6/1996 |
| JP | 08-208424 | | 8/1996 |
| JP | 09-143050 | | 6/1997 |
| JP | 11-012122 | | 1/1999 |
| JP | 11-029467 | | 2/1999 |
| JP | 2000-016917 | | 1/2000 |
| JP | 2000-038334 | | 2/2000 |
| JP | 2000-302659 | * | 10/2000 |
| JP | 2000-327557 | | 11/2000 |
| JP | 2004-331593 | | 11/2004 |
| JP | 2006-327966 | | 7/2006 |
| JP | 2006-327966MT | * | 12/2006 |
| RU | 2 175 546 | | 9/1997 |
| WO | WO 2006/065522 A2 | | 6/2006 |

OTHER PUBLICATIONS

Both et al. in Archives of Dermatological Research (2002) 293: 569-575.*
International Search Report dated Jul. 19, 2007.
Notice of Reason for Rejection issued Jul. 31, 2012 to corresponding Japanese Patent Application No. 2008-522332.
Extended European Search Report issued in corresponding European Patent Application No. 07742216.0, on Dec. 4, 2012.

* cited by examiner

*Primary Examiner* — Dennis Heyer
(74) *Attorney, Agent, or Firm* — Knobbe, Martens, Olson & Bear LLP

(57) ABSTRACT

Disclosed is a skin external preparation containing a triterpenic acid typified by ursolic acid. For obtaining a skin external preparation having excellent storage stability by improving the dissolution stability of the triterpenic acid and the like, 4-alkylresorcinol such as 4-n-butylresorcinol is added into a skin external preparation containing a triterpenic acid and the like such as benzyl ursolate.

16 Claims, No Drawings

SKIN EXTERNAL PREPARATION CONTAINING TRITERPENIC ACID

CROSS-REFERENCE TO RELATED APPLICATIONS

This application is the U.S. National Phase under 35 U.S.C. §371 of International Application PCT/JP2007/058781, filed Apr. 24, 2007, which was published in a non-English language, which claims priority to JP Application No. 2006-169113, filed Jun. 19, 2006.

TECHNICAL FIELD

The present invention relates to a skin external preparation, such as a cosmetic, or a medicine for external application to skin, containing a triterpenic acid.

BACKGROUND ART

Triterpenic acids including ursolic acid are known to have various physiological activities such as antioxidant effect, anti-inflammatory effect, melanin production inhibitory effect, and collagen reconstruction effect, and there are known techniques for using a triterpenic acid as an active ingredient of the skin external preparation such as cosmetics (for example, Patent Documents 1, 2, 3 and 4). However, the triterpenic acid has poor solubility in an oily component and an aqueous component, and has a problem of precipitation of the triterpenic acid when the preparation is stored for a long period of time. Lack of storage stability of the skin external preparation containing the triterpenic acid is not preferred, because the above-mentioned physiological activities are reduced. Under such circumstances, there has been studied a method of improving solubility of the triterpenic acid in the oily component through derivatization of the triterpenic acid into an ester or ether (Patent Document 5). The method provides an effect of improving the solubility of the triterpenic acid in some degree, but the effect is not enough to prevent the precipitation of the triterpenic acid when the preparation is stored for a long period of time. In order to solve such problems, a technique of using aliphatic saturated alcohols having 12 to 24 carbon atoms or the like in combination has been developed (Patent Document 6). The technique provides the effect of improving the solubility of the triterpenic acid in some degree, but in the case where a preparation containing a triterpenic acid at a concentration of as high as 0.1% by mass or more is stored for a long period of time under a low-temperature condition, there may cause crystals to appear. That is, techniques for further improving the solubility and storage stability of the skin external preparation, containing the triterpenic acid have been required.

Meanwhile, 4-n-butylresorcinol is known to have a strong inhibitory effect of tyrosinase activity and to act as a very effective skin-whitening agent (Patent Document 7), and is used as a material of cosmetics. However, it has not been known that a 4-alkylresorcinol such as 4-n-butylresorcinol has the effect to enhance long-term storage stability of the triterpenic acid. Also, it has not been known that a 4-alkylresorcinol can be actually blended with the triterpenic acid in the skin external preparation.

Patent Document 1: JP 8-165231 A
Patent Document 2: JP 8-208424 A
Patent Document 3: JP 11-12122 A
Patent Document 4: JP 2000-302659 A
Patent Document 5: JP 09-143050 A
Patent Document 6: JP 2004-331593 A
Patent Document 7: JP 02-49715 A

DISCLOSURE OF THE INVENTION

An object of the present invention is to provide techniques for enhancing solubility and improving storage stability of a triterpenic acid and/or a derivative thereof (hereinafter, also referred to as triterpenic acid or the like) in a preparation containing the triterpenic acid or the like. In particular, an object of the present invention is to provide means for improving long-term storage stability and stability under a low-temperature storage condition of a preparation containing the triterpenic acid or the like at a concentration of as high as, for example, 0.1% by mass or more.

The inventors of the present invention found that addition of a 4-alkylresorcinol such as 4-n-butylresorcinol and/or a salt thereof (hereinafter, also referred to as 4-alkylresorcinol or the like) to a skin external preparation containing a triterpenic acid or the like such as benzyl ursolate at a relatively high concentration can prevent precipitation of the triterpenic acid or the like even when the preparation is stored for a long period of time under the low-temperature condition, thus completing the present invention. That is, the present invention relates to the following technologies.

[1] A skin external preparation including component (1) a triterpenic acid and/or a derivative thereof; and component (2) a 4-alkylresorcinol and/or a salt thereof.

[2] A skin external preparation according to the item [1], in which the component (1) is ursolic acid and/or a derivative thereof.

[3] A skin external preparation according to the item [1], in which the component (1) is triterpenic acid benzyl ester.

[4] A skin external preparation according to the item [1], in which the component (1) is benzyl ursolate.

[5] A skin external preparation according to any one of the items [1] to [4], in which the component (2) is a 4-n-butylresorcinol and/or a salt thereof.

[6] A skin external preparation according to any one of the items [1] to [5], in which a content of the component (1) is 0.1 to 5% by mass.

[7] A skin external preparation according to any one of the items [1] to [6], further including a branched fatty acid.

[8] A skin external preparation according to the item [7], in which the branched fatty acid is isostearic acid.

[9] A skin external preparation according to any one of the items [1] to [8], in which the skin external preparation is a cosmetic.

BEST MODE FOR CARRYING OUT THE INVENTION

<1> Triterpenic Acid and/or Derivative Thereof as Essential Component of the Skin External Preparation of the Present Invention A skin external preparation of the present invention contains a triterpenic acid and/or a derivative thereof (component 1). The triterpenic acid is not particularly limited as long as the triterpenic acid can be used in the field of skin external preparations such as cosmetics. Preferable examples thereof include ursolic acid, oleanolic acid, betulinic acid, and asiatic acid ((2α,3β,4α)-2,3,23-trihydroxyurs-12-en-ursolic acid, (2α,3β,4α)-2,3,23-trihydroxyurs-12-en-28-oic acid). Of those, the ursolic acid is particularly preferably exemplified.

The triterpenic acid can be obtained in accordance with a conventional method, and may be extracted from a plant or may be a commercially-available product. For example, ursolic acid is contained in fruits of bearberry, apple, and cherry, leaves of various plants, etc.; oleanolic acid is contained in olive leaves, apple peels, clove buds, etc.; betulinic acid is contained in dogwood barks, pomegranate peels, jujube, etc.; and asiatic acid is contained in Indian Pennywort, etc. Therefore, the triterpenic acid can be used by concentrating and purifying extracts of those plants. Meanwhile, examples of the commercialized product of ursolic acid include Ursolic Acid (manufactured by Tokyo Chemical Industry Co., Ltd.); examples of the commercialized product of oleanolic acid include Oleanolic Acid (manufactured by Sigma-Aldrich Corporation); examples of the commercialized product of betulinic acid include Betulinic Acid (Sigma-Aldrich Corporation); and examples of the commercialized product of asiatic acid include Asiatic Acid (Sigma-Aldrich Corporation).

The derivative of the triterpenic acid is not particularly limited as long as the derivative of the triterpenic acid has the physiological activity of the triterpenic acid. Specific examples of the derivative of the triterpenic acid include salts of triterpenic acid, esters of triterpenic acid, amides of triterpenic acid, and ethers of triterpenic acid. Salts of triterpenic acid and esters of triterpenic acid are preferably exemplified in the skin external preparation of the present invention. Preferable examples of the esters include methyl ursolate, ethyl ursolate, propyl ursolate, butyl ursolate, benzyl ursolate, methyl oleanolate, ethyl oleanolate, propyl oleanolate, butyl oleanolate, benzyl oleanolate, methyl betulinate, ethyl betulinate, propyl betulinate, butyl betulinate, benzyl betulinate, methyl asiatate, ethyl asiatate, propyl asiatate, butyl asiatate, and benzyl asiatate. Of those, benzyl ursolate is particularly preferred. This is because the benzyl ursolate is excellent in storage stability and also, high physiological activity of ursolic acid can be obtained. In addition, the salt of triterpenic acid can be used without particular limitation as long as the salt is physiologically permitted. Examples of the salt include alkali metal salts such as a sodium salt and a potassium salt, alkali earth metal salts such as a calcium salt and a magnesium salt, ammonium salts, organic amine salts such as a triethyl amine salt and a triethanol amine salt, and basic amino acid salts such as an arginine salt and a lysine salt.

The derivative of the triterpenic acid can be produced in accordance with a conventional method. For example, a benzyl ester of a triterpenic acid can be produced by: converting the triterpenic acid into a triethylamine salt; and reacting the resultant salt with benzyl chloride. Meanwhile, esters of a triterpenic acid can be obtained by a reaction of the triterpenic acid with an alcohol in the presence of a mineral acid catalyst.

The skin external preparation of the present invention may contain one of the triterpenic acids and derivatives thereof alone or may contain two or more of them in combination.

The content of the triterpenic acid or the like in the skin external preparation of the present invention is not particularly limited as long as the physiological activity of the triterpenic acid or the like can be obtained. Even in the case of the skin external preparation of the present invention containing a triterpenic acid or the like at a content of 0.1% by mass or more in total, precipitation of crystals is suppressed, resulting in high stability. Therefore, the excellent effect of the present invention can be achieved in the skin external preparation containing a triterpenic acid or the like at a content of 0.1% by mass to 5% by mass, preferably 0.2% by mass to 3% by mass, more preferably 0.3% by mass to 3% by mass in total.

<2> 4-alkylresorcinol and/or Salt Thereof as Essential Component of the Skin External Preparation of the Present Invention The skin external preparation of the present invention is characterized by containing a 4-alkylresorcinol and/or a salt thereof (component 2). The alkyl group in the 4-alkylresorcinol is preferably an alkyl group having 3 to 10 carbon atoms, more preferably an alkyl group having 3 to 8 carbon atoms. Specific examples of the alkyl group include n-propyl, isopropyl, n-butyl, isobutyl, sec-butyl, tert-butyl, amyl, n-hexyl, cyclohexyl, octyl, and isooctyl groups. The skin external preparation of the present invention particularly preferably contains 4-n-butylresorcinol. The 4-alkylresorcinol such as 4-n-butylresorcinol is a known substance and can be produced in accordance with a conventional method such as the method described in Lille, J.; Bitter, L. A.; Peiner, V. Trudy-Nauchono-Issledovatel' skii Institut Slantsev (1969), No. 18, 127-34. That is, examples of a method of producing 4-n-butylresorcinol includes: a method including condensing resorcin and butanoic acid in the presence of zinc chloride and reducing the resultant product with zinc amalgam/hydrochloric acid; and a method including condensing resorcin and n-butyl alcohol at 200 to 400° C. In this method, if another n-hexyl alcohol or the like is substituted for n-butyl alcohol, another 4-alkylresorcinol can be synthesized. In addition, 4-n-hexylresorcinol is commercially available from Aldrich Chemical Company, Inc., and the product may be purchased and used.

In addition, the salts of 4-alkylresorcinol may be generally used in cosmetics and physiologically permitted. Examples of the salt include salts of alkali metals such as sodium and potassium, salts of alkali earth metals such as calcium and magnesium, ammonium salts, salts of organic amines such as triethyl amine and triethanol amine, and salts of basic amino acid such as lysine and arginine.

The skin external preparation of the present invention may contain one of the 4-alkylresorcinols and salts thereof alone or may contain two or more of them in combination.

The content of the 4-alkylresorcinol or the like in the skin external preparation of the present invention is preferably 0.01% by mass or more, more preferably 0.05% by mass or more, further preferably 0.1% by mass or more in total with respect to the total amount of the preparation. The upper limit is preferably 3% by mass or less, more preferably 1% by mass or less, further preferably 0.5% by mass or less. The reason is that if the content is too low, the effect of the present invention may not be exerted, while if the content is too high, the effect may reach a plateau.

The content ratio of a triterpenic acid and/or a derivative thereof to a 4-alkylresorcinol and/or a salt thereof is preferably 5:1 to 1:10, more preferably 5:1 to 1:5.

<3> Branched Fatty Acid as Preferable Component of the Skin External Preparation of the Present Invention The skin external preparation of the present invention preferably further contains a branched fatty acid in addition to the above-mentioned essential components. The fatty acid further improves long-term storage stability of the skin external preparation of the present invention. The branched fatty acid is preferably a branched fatty acid having 12 to 30 carbon atoms, particularly preferably isostearic acid. The branched fatty acid may be contained as a free carboxylic acid or as a salt. The salt may be generally used in a cosmetic and is physiologically acceptable. Preferable examples thereof include: salts of alkaline metals such as sodium and potassium; salts of alkaline earth metals such as calcium and magnesium; ammonium salts; salts of organic amines such as triethylamine and triethanolamine; and salts of basic amino acids such as lysine and arginine. Although the content of the branched fatty acid is not particularly limited, the content is 0.1 to 30% by mass, preferably 1 to 10% by mass.

<4> Skin External Preparation of the Present Invention

The skin external preparation of the present invention contains a triterpenic acid or the like that is poorly soluble in water, and the preparation is preferably in an oil-based formulation containing an oily component or a polyol as a main component, or in an essence-type formulation containing a large amount of polyols. Meanwhile, a 4-alkylresorcinol or the like is soluble both in an oily component and water, and the preparation is preferably in the form of an emulsion containing an aqueous component including water and an oily component.

Although the skin external preparation of the present invention may be applied to any of preparations for cosmetics and medicines for external application to skin, the skin external preparation is particularly suitably used for cosmetics. In the case of using 4-n-butylresorcinol or the like, the preparation is more desirably applied to cosmetics, in particular, quasi-drugs.

In addition, the skin external preparation of the present invention can be used for the purposes of treatment, prevention, or amelioration of specific skin diseases or symptoms, depending on various physiological activities of the triterpenic acid or the like. For example, the skin external preparation containing ursolic acid or a derivative of ursolic acid such as benzyl ursolate has ability to reconstruct collagen fiber bundles; therefore, the preparation can be used as an anti-wrinkle cosmetic. The skin external preparation containing oleanolic acid or a derivative thereof has ability to ameliorate acne skin; therefore, the preparation can be used as a cosmetic for acne skin or oily skin.

The skin external preparation of the present invention may contain an optional component that is generally used in the skin external preparation in addition to the above-mentioned essential components. Such an optional component is not particularly limited as long as the component does not inhibit the effect of the present invention. Examples thereof include hydrocarbons, silicones, esters, fatty acids, triglycerides, polyols, organic powders, inorganic powders, surfactants, thickeners, vitamins, steroids, antiseptic agents, and ultraviolet absorbers. Those optional components may be blended in amounts not enough to inhibit the effect of the present invention.

Examples of the hydrocarbons include squalane, a liquid paraffin, a light liquid isoparaffin, a heavy liquid isoparaffin, a microcrystalline wax, and a hard paraffin.

Examples of the silicones include dimethicone, phemethicone, cyclomethicone, amodimethicone, and modified polysiloxanes such as a polyether-modified polysiloxane.

Examples of the esters include octyldodecyl oleate, cetyl isooctanate, cetyl stearate, isopropyl myristate, hexyldecyl isostearate, neopentylglycol diisostearate, sorbitan sesquistearate, diisopropyl adipate, di-2-ethylhexyl sebacate, cetyl lactate, diisostearyl malate, ethylene glycol di-2-ethylhexanoate, neopentyl glycol dicaprate, glycerin di-2-heptyl undacanoate, glycerin tri-2-ethylhexanoate, trimethylolpropane tri-2-ethylhexanoate, trimethylolpropane triisostearate, pentaerythritol tetra-2-ethylhexanoate, and diester of dimer acid.

Examples of the aliphatic acids include oleic acid, isostearic acid, lauric acid, myristic acid, palmitic acid, isopalmitic acid, stearic acid, behenic acid, and undecylenic acid.

Examples of the triglycerides include castor oil, coconut oil, hydrogenated coconut oil, camellia oil, wheat germ oil, isostearic acid triglyceride, isoocatanoic acid triglyceride, 2-ethylhexanoic acid triglyceride, and olive oil.

Examples of the polyols include 1,3-butanediol, 1,2-butanediol, glycerin, diglycerin, dipropylene glycol, polyethylene glycol, 1,2-pentanediol, hexylene glycol, and isoprene glycol.

Examples of the organic powders include a crystalline cellulose, a crosslinking methyl polysiloxane, a polyethylene powder, and an acrylic resin powder.

Examples of the inorganic powders include talc, mica, sericite, magnesium carbonate, calcium carbonate, titanium dioxide, iron oxide, iron blue, ultramarine blue, titanium dioxide coated mica, titanium dioxide coated sericite, and silica, all of which may be subjected to surface treatment.

Examples of the surfactant include: anionic surfactants such as aliphatic soap (including sodium laurate and sodium palmitate), potassium lauryl sulfate, and triethanol amine ether alkyl sulfate; cationic surfactants such as chlorinate stearyl trimethyl ammonium, chlorinated bezalkonium, and lauryl amine oxide; and amphoteric surfactants such as imidazoline-based amphoteric surfactants (including 2-cocoyl-2-imidazolinium hydroxide-1-carboxyethyloxy-2-sodium salt), betaine-based surfactants (including alkyl betaine, amide betaine, and sulfobetaine), and acylmethyl taurine; nonionoic surfactants such as sorbitan aliphatic esters (including sorbitan monostearate and sorbitan sesquioleate), glycerin aliphatic acids (including glycerin monostearate), propylene glycol aliphatic esters (including propylene glycol monostearate), cured castor oil derivatives, glycerin alkyl ether, POE sorbitan aliphatic esters (including POE sorbitan monolaurate, POE sorbitan monooleate, and polyoxyethylene sorbitan monostearate), POE sorbit aliphatic esters (including POE-sorbit monolaurate), POE glycerin aliphatic esters (including POE glycerin monoisostearate), POE aliphatic esters (including POE monolaurate, POE monooleate, and POE distearate), POE alkyl ethers (including POE cetyl ether and POE 2-octyldodecyl ether), POE alkyl phenyl ethers (including POE nonylphenyl ether), Pluronic (registered mark), POE•POP alkyl ethers (including POE•POP 2-decyl tetradecyl ether), Tetronic (registered mark), POE castor oil•cured castor oil derivatives (including POE castor oil and POE cured castor oil), sucrose aliphatic esters, and alkyl glucoside.

Examples of the thickener include an acrylate/alkyl methacrylate copolymer and/or its salts, a carboxyvinyl polymer and/or its salts, alginate, a polyol ester of alginic acid, xanthan gum, and hydroxypropyl cellulose.

Examples of the vitamins include retinol, retinoic acid, tocopherol, riboflavin, pyridoxin, ascorbic acid, and ascorbic phosphate.

Examples of the steroid include steroids such as estradiol, ethinyl estradiol, and estriol.

Examples of the antiseptic agent include phenoxy ethanol, parabens, hibitane gluconate, and benzalkonium chloride. Examples of the UV absorber include; dimethyl amino benzoates, cinnamates, and benzophenones.

In the following, the present invention will be described in more detail by way of examples, but it is to be understood that the present invention is not limited to those examples.

EXAMPLES

Referential Example

Production of Benzyl Ursolate 5 g of ursolic acid was dissolved in 300 ml of dimethylformamide, and 63 ml of triethylamine was added thereto. Then, 20 g of benzyl chloride was added thereto, and the whole was stirred at 50° C. for 1 hour and concentrated under reduced pressure, followed by purification by silica gel chromatography (elution solvent; chloroform:methanol=100:0 to 80:20), to thereby obtain benzyl ursolate.

Example 1

According to the following prescription, a cream of Example 1, which is the skin external preparation of the present invention, was prepared. The components described in (A) were mixed and dissolved by heating at 80° C. In the same way as above, the components described in (B) were dissolved uniformly and heated at 80° C., and the mixture (A) was added to the mixture (B) with stirring, followed by cooling to 40° C. with stirring using a homomixer. The components described in (C) heated to 40° C. were added to the resultant mixture, and the whole was cooled to room temperature with stirring.

In addition, in Comparative Example 1, the same procedures as in Example 1 were repeated except that purified water was substituted for 4-n-butylresorcinol; in Comparative Example 2, the same procedures as in Example 1 were repeated except that purified water described in (C) was increased instead of removed benzyl ursolate; and in Comparative Example 3, purified water described in (C) was increased instead of removed 4-n-butylresorcinol and benzyl ursolate.

| (A) | |
|---|---|
| Cetyl isooctanate | 2.0 mass % |
| 2-ethyl hexanoic acid triglyceride | 10.0 mass % |
| Di(isostearyl/phytosteryl/cetyl/stearyl/behenyl) dimer dilinolate "Plandool" (manufactured by Nippon Fine Chemical Co., Ltd.) | 1.0 mass % |
| Behenic acid | 1.0 mass % |
| Squalane | 2.0 mass % |
| Dimethicone | 1.0 mass % |
| Cetyl stearate | 0.5 mass % |
| Isostearic acid | 1.0 mass % |
| Benzyl ursolate | 0.2 mass % |
| Sorbitan sesquistearate | 1.5 mass % |
| POE(45) monostearate | 1.0 mass % |
| (B) | |
| 1,3-butanediol | 5.0 mass % |
| Glycerin | 10.0 mass % |
| 1,2-butanediol | 5.0 mass % |
| 4-n-butylresorcinol | 0.1 mass % |
| Carboxyvinyl polymer | 0.2 mass % |
| Purified water | 49.0 mass % |
| (C) | |
| Purified water | 8.8 mass % |
| Potassium hydroxide | 0.7 mass % |

Test Example 1

Test on Dissolution Stability

Samples were left to stand in a low temperature aging box (the samples were stored at −10° C. for 24 hours, heated to 5° C. over 24 hours, stored at 5° C. for 24 hours, and cooled to −10° C. over 24 hours; the procedure was defined as one cycle and repeated) for three months and returned to the state of room temperature, and 0.10 g of each of the creams of Example 1 and Comparative Examples 1 to 3 was collected and spread on black plates using a spatula. Then, the fine precipitates contained in the samples were observed and counted under a microscope. The term "fine precipitates" refers to crystals that can be observed under a microscope and have sizes of about 5 to 50 μm. Note that the fine precipitates having such sizes are not large enough to give a feel to the skin when cosmetics or the like are used, but such crystals may grow to those having larger sizes. Therefore, in the skin external preparation containing a triterpenic acid, it is important to suppress appearance of such fine precipitates.

The results are shown in Table 1.

TABLE 1

| | Number of fine precipitates |
|---|---|
| Example 1 | 0 |
| Comparative Example 1 | 41 |
| Comparative Example 2 | 0 |
| Comparative Example 3 | 0 |

In the case of the sample containing benzyl ursolate and 4-n-butylresorcinol prepared in Example 1, fine precipitates were not observed. On the other hand, in the case of the sample containing benzyl ursolate and not containing 4-n-butylresorcinol prepared in Comparative Example 1, many fine precipitates were observed. In the cases of the sample not containing benzyl ursolate and containing 4-n-butylresorcinol prepared in Comparative Example 2 and the sample not containing both of benzyl ursolate and 4-n-butylresorcinol prepared in Comparative Example 3, no fine precipitates were observed.

The results revealed that 4-n-butylresorcinol could enhance dissolution stability of benzyl ursolate. That is, it was found that the skin external preparation of the present invention was excellent in storage stability under a low-temperature condition.

Examples 2 and 3

According to the following prescription, a cream of Example 2, which is the skin external preparation of the present invention, was prepared. That is, a mixture obtained by mixing the components described in (B) and dissolving them by heating at 80° C. was added to a mixture obtained by mixing the components described in (A) and heating them to 80° C., and the components described in (C) were heated to 80° C. and added thereto, followed by stirring. The components described in (D) were mixed therein at 40° C., and the whole was stirred and cooled.

In Comparative Example 4, the same procedures as in Example 2 were repeated except that purified water was substituted for 4-n-butylresorcinol. In Example 3, the same procedures as in Example 2 were repeated except that 4-n-hexylresorcinol (purchased from Aldrich) was substituted for 4-n-butylresorcinol.

| (A) | |
|---|---|
| Alginic acid propylene glycol ester "Kimiloid BF" (manufactured by KIMICA Corporation) | 1.0 mass % |
| Sodium alginate "Kimica Algine KP" (manufactured by KIMICA Corporation) | 0.5 mass % |
| 1,3-butanediol | 6.0 mass % |
| Glycerin | 5.0 mass % |
| Phenoxy ethanol | 0.3 mass % |
| 4-n-butylresorcinol | 0.3 mass % |
| Purified water | 38.0 mass % |

-continued

| (B) | |
|---|---|
| 2-ethyl hexanoic acid triglyceride | 8.0 mass % |
| Ursolic acid | 0.1 mass % |
| Isostearic acid | 1.0 mass % |
| Di(isostearyl/phytosteryl/cetyl/stearyl/behenyl) dimer dilinolate "Plandool H" (manufactured by Nippon Fine Chemical Co., Ltd.) | 0.5 mass % |
| Sorbitan monostearate "Sorbon S60" (manufactured by TOHO Chemical Industry Co., Ltd.) | 0.5 mass % |
| POE(25) monostearate | 0.5 mass % |
| Tri(caprylic acid/capric acid/myristic acid/stearic acid)triglyceride "Salacos 334" (manufactured by The Nisshin OilliO Group, Ltd.) | 2.7 mass % |
| Behenic acid | 0.3 mass % |
| Squalane | 1.0 mass % |
| Di(phytosteryl/2-octyldodecyl) N-lauroyl glutamate "Eldew PS-203" (manufactured by AJINOMOTO Co., Inc.) | 0.5 mass % |
| Methyl polysiloxane | 1.0 mass % |
| (C) | |
| Calcium chloride | 0.05 mass % |
| Purified water | 3.5 mass % |
| (D) | |
| Potassium hydroxide | 0.1 mass % |
| Purified water | 29.15 mass % |

Test Example 2

Test on Dissolution Stability

The creams prepared in Example 2, Comparative Example 4, and Example 3 were stored in a low temperature aging box for three months in the same way as in Test Example 1, returned to the state of room temperature, and spread on black plates. The fine precipitates were counted. The results are shown in Table 2.

TABLE 2

| | Number of fine precipitates |
|---|---|
| Example 2 | 0 |
| Example 3 | 0 |
| Comparative Example 4 | 29 |

In the case of the sample containing ursolic acid and 4-n-butylresorcinol prepared in Example 2, fine precipitates were not observed. On the other hand, in the case of the sample containing ursolic acid and not containing 4-n-butylresorcinol prepared in Comparative Example 4, many fine precipitates were observed. In addition, in the case of the sample containing ursolic acid and 4-n-hexylresorcinol prepared in Example 3, no fine precipitates were observed.

Examples 4 and 5

According to the following prescription, a cream of Example 4, which is the skin external preparation of the present invention, was prepared in the same way as in Example 1. In Comparative Example 5, the same procedures as in Example 4 were repeated except that purified water was substituted for 4-n-butylresorcinol. In Example 5, the same procedures as in Example 4 were repeated except that purified water described in (C) was increased instead of removed isostearic acid described in (A).

| (A) | |
|---|---|
| Cetyl isooctanate | 2.0 mass % |
| 2-ethyl hexanoic acid triglyceride | 10.0 mass % |
| Tri(caprylic acid/capric acid/myristic acid/stearic acid)triglyceride "Salacos 334" (manufactured by The Nisshin OilliO Group, Ltd.) | 1.0 mass % |
| Behenic acid | 1.0 mass % |
| Squalane | 2.0 mass % |
| Dimethicone | 1.0 mass % |
| Cetyl stearate | 0.5 mass % |
| Isostearic acid | 1.0 mass % |
| Benzyl ursolate | 0.5 mass % |
| Sorbitan sesquistearate | 1.5 mass % |
| POE(45) monostearate | 1.0 mass % |
| (B) | |
| 1,3-butanediol | 5.0 mass % |
| Glycerin | 10.0 mass % |
| 1,2-butanediol | 5.0 mass % |
| 4-n-butylresorcinol | 0.1 mass % |
| Carboxyvinyl polymer | 0.2 mass % |
| Purified water | 49.0 mass % |
| (C) | |
| Purified water | 8.5 mass % |
| Potassium hydroxide | 0.7 mass % |

Examples 6 and 7

According to the following prescription, a cream of Example 6, which is the skin external preparation of the present invention, was prepared in the same way as in Example 1. In Example 7, the same procedures as in Example 6 were repeated except that oleanolic acid was substituted for betulinic acid. In Comparative Example 6, the same procedures as in Example 6 were repeated except that purified water was substituted for 4-n-butylresorcinol. In Comparative Example 7, the same procedures as in Example 7 were repeated except that purified water was substituted for 4-n-butylresorcinol.

| (A) | |
|---|---|
| Cetyl isooctanate | 2.0 mass % |
| 2-ethyl hexanoic acid triglyceride | 10.0 mass % |
| Tri(caprylic acid/capric acid/myristic acid/stearic acid)triglyceride (Salacos 334" (manufactured by The Nisshin OilliO Group, Ltd.) | 1.0 mass % |
| Behenic acid | 1.0 mass % |
| Squalane | 2.0 mass % |
| Dimethicone | 1.0 mass % |
| Cetyl stearate | 0.5 mass % |
| Isostearic acid | 1.0 mass % |
| Betulinic acid | 0.5 mass % |
| Sorbitan sesquistearate | 1.5 mass % |
| POE(45) monostearate | 1.0 mass % |
| (B) | |
| 1,3-butanediol | 20.0 mass % |
| 4-n-butylresorcinol | 0.3 mass % |
| Carboxyvinyl polymer | 0.2 mass % |
| Purified water | 48.8 mass % |
| (C) | |
| Purified water | 8.5 mass % |
| Potassium hydroxide | 0.7 mass % |

Test Example 3

Test on Dissolution Stability

In the same way as in Test Example 1, the creams prepared in Examples 4 to 7 and Comparative Examples 5 to 7 were stored in a low temperature aging box for three months, returned to the state of room temperature, and spread on black plates. The fine precipitates were counted. The results are shown in Table 3.

TABLE 3

|  | Number of fine precipitates |
|---|---|
| Example 4 | 0 |
| Example 5 | 2 |
| Example 6 | 0 |
| Example 7 | 0 |
| Comparative Example 5 | 37 |
| Comparative Example 6 | 32 |
| Comparative Example 7 | 34 |

In the case of the sample of Example 4 containing benzyl ursolate, 4-n-butylresorcinol, and isostearic acid, no fine precipitates were observed. On the other hand, in the case of the sample of Comparative Example 5 containing benzyl ursolate and isostearic acid and not containing 4-n-butylresorcinol, many fine precipitates were observed. Meanwhile, in the case of the sample of Example 5 containing benzyl ursolate and 4-n butylresorcinol and not containing isostearic acid, a small amount of fine precipitates were observed. In the cases of the sample of Example 6 containing betulinic acid and 4-n-butylresorcinol and the sample of Example 7 containing oleanolic acid and 4-n-butylresorcinol, no fine precipitates were observed. On the other hand, in the cases of the samples of Comparative Examples 6 and 7 not containing 4-n-butylresorcinol, fine precipitates were observed.

The results reveal that isostearic acid has an effect to enhance dissolution stability of a triterpenic acid such as ursolic acid, betulinic acid, or oleanolic acid and can enhance storage stability of the skin external preparation containing a triterpenic acid at a high concentration.

Example 8

According to the following prescription, the respective components were dissolved uniformly at 80° C. and cooled to room temperature, to thereby prepare an oil-based essence of Example 8. Further, in Comparative Example 8, the above-mentioned procedures were repeated except that squalan was substituted for 4-n-butylresorcinol.

| | |
|---|---|
| Cetyl isooctanate | 2.0 mass % |
| 2-ethyl hexanoic acid triglyceride | 15.0 mass % |
| Squalane | 3.0 mass % |
| "Silicone KSG-16" (manufactured by Shin-Etsu Chemical Co., Ltd.) | 10.0 mass % |
| Decamethyl cyclopentane siloxane (manufactured by Shin-Etsu Chemical Co., Ltd.) | 30.0 mass % |
| Isostearic acid | 1.0 mass % |
| Benzyl ursolate | 1.0 mass % |
| Sorbitan sesquistearate | 1.5 mass % |
| POE(25) monostearate | 1.0 mass % |
| 1,3-butanediol | 25.0 mass % |
| Glycerin | 5.0 mass % |
| 1,2-butanediol | 5.0 mass % |
| 4-n-butylresorcinol | 0.5 mass % |

Test Example 4

Test on Dissolution Stability

In the same way as in Test Example 1, the oil-based essences prepared in Example 8 and Comparative Example 8 were stored in a low temperature aging box for three months, returned to the state of room temperature, and spread on black plates. The fine precipitates were counted. The results are shown in Table 4.

TABLE 4

|  | Number of fine precipitates |
|---|---|
| Example 8 | 0 |
| Comparative Example 8 | 19 |

In the case of the sample of Example 8 of the present invention containing 4-n-butylresorcinol, no fine precipitates were observed. On the other hand, in the case of the sample of Comparative Example 8 not containing 4-n-butylresorcinol, many fine precipitates were observed. The results reveal that 4-n-butylresorcinol can enhance dissolution stability of benzyl ursolate even if the 4-n-butylresorcinol is contained in the skin external preparation in the form of an oil-based essence.

INDUSTRIAL APPLICABILITY

In the skin external preparation of the present invention containing a triterpenic acid or the like and a 4-alkylresorcinol or the like, the triterpenic acid or the like has excellent solubility. In particular, even when the skin external preparation containing a triterpenic acid or the like at a concentration of as high as 0.1% by mass or more is stored under a low-temperature condition for a long period of time, the triterpenic acid or the like is not precipitated.

What is claimed is:

1. A skin external preparation, comprising:
   component (1) 1.0 wt % or less of a triterpenic acid and/or an ester, amide, ether or salt derivative thereof, provided that the content of the triterpenic acid and/or the derivative thereof is not 0; and
   component (2) 0.1 to 0.5 wt % of a 4-alkylresorcinol and/or a salt thereof.

2. A skin external preparation according to claim 1, wherein component (1) is ursolic acid and/or an ester, amide, ether or salt derivative thereof.

3. A skin external preparation according to claim 1, wherein component (1) is triterpenic acid benzyl ester.

4. A skin external preparation according to claim 1, wherein component (1) is benzyl ursolate.

5. A skin external preparation according to claim 1, wherein component (2) is selected from the group consisting of 4-n-butylresorcinol, 4-n-hexylresorcinol, 4-cyclohexylresorcinol and salts thereof.

6. A skin external preparation according to claim 1, wherein the content of component (1) is 0.1 to 1 wt % by mass.

7. A skin external preparation according to claim 1, further comprising a branched fatty acid.

8. A skin external preparation according to claim 7, wherein the branched fatty acid is isostearic acid.

9. A skin external preparation according to claim 1, wherein the skin external preparation is a cosmetic.

10. A skin external preparation according to claim 2, wherein component (2) is selected from the group consisting of 4-n-butylresorcinol, 4-n-hexylresorcinol, 4-cyclohexylresorcinol and salts thereof.

11. A skin external preparation according to claim 3, wherein component (2) is selected from the group consisting of 4-n-butylresorcinol, 4-n-hexylresorcinol, 4-cyclohexylresorcinol and salts thereof.

12. A skin external preparation according to claim 4, wherein component (2) is selected from the group consisting of 4-n-butylresorcinol, 4-n-hexylresorcinol, 4-cyclohexylresorcinol and salts thereof.

13. A skin external preparation according to claim 5, wherein the content of component (1) is 0.1 to 1 wt % by mass.

14. A skin external preparation according to claim 5, further comprising a branched fatty acid.

15. A skin external preparation according to claim 14, wherein the branched fatty acid is isostearic acid.

16. A skin external preparation according to claim 5, wherein the skin external preparation is a cosmetic.

* * * * *